United States Patent [19]

Huang et al.

[11] Patent Number: 5,644,239

[45] Date of Patent: Jul. 1, 1997

[54] METHOD AND APPARATUS FOR SENSING THE CONDITION OF A FLUID

[75] Inventors: Joseph Y. Huang; Cheng-Foo Chen, both of Troy, Mich.

[73] Assignee: American Systems Technology, Inc., Troy, Mich.

[21] Appl. No.: 228,561

[22] Filed: Apr. 15, 1994

[51] Int. Cl.⁶ ................................................ G01N 27/02
[52] U.S. Cl. ...................... 324/439; 324/441; 324/698; 324/721; 324/71.1; 73/61.74
[58] Field of Search ............................ 324/693, 698, 324/441, 439, 71.1, 713, 721; 73/61.76, 61.74; 340/631

[56] References Cited

U.S. PATENT DOCUMENTS

| | | | |
|---|---|---|---|
| 1,721,374 | 7/1929 | Dautsizen | 324/721 |
| 2,548,763 | 4/1951 | Askevold | 324/441 |
| 2,752,566 | 6/1956 | Quinton | 324/65 |
| 3,515,988 | 6/1970 | Shawhan | 324/441 |
| 3,836,849 | 9/1974 | Coulter et al. | 324/71.1 |
| 4,029,554 | 6/1977 | Ellison | 204/1 T |
| 4,686,857 | 8/1987 | Kato | 73/304 R |
| 4,733,556 | 3/1988 | Meitzler et al. | 73/64 |
| 4,744,870 | 5/1988 | Kauffman | 204/1 T |
| 4,764,258 | 8/1988 | Kauffman | 201/1 T |
| 5,028,144 | 7/1991 | Klein | 374/44 |
| 5,059,891 | 10/1991 | Bohandy et al. | 324/71.6 |
| 5,194,910 | 3/1993 | Kirkpatrick, Jr. et al. | 356/70 |
| 5,272,444 | 12/1993 | Cox | 324/698 |

FOREIGN PATENT DOCUMENTS

| | | | |
|---|---|---|---|
| 0080632 | 6/1983 | European Pat. Off. | 324/698 |
| 0168322 | 9/1984 | Japan | 324/698 |
| 403284863 | 12/1991 | Japan | 324/721 |
| 1355918 | 11/1987 | U.S.S.R. | 324/670 |

*Primary Examiner*—Vinh P. Nguyen
*Assistant Examiner*—Diep Do
*Attorney, Agent, or Firm*—Gifford, Krass, Groh, Sprinkle, Patmore, Anderson & Citkowski

[57] ABSTRACT

A method and apparatus for determining the condition of a fluid used in a process, such as a lubricating oil used in an internal combustion engine. A sample of the fluid is heated to an elevated temperature, a measurement is taken of an electrical characteristic of the fluid at that first temperature, the fluid is heated still further, and the aforesaid electrical characteristic is measured again. The two measured values of the electrical characteristic are used to calculate a quality parameter which, when compared with quality parameter values corresponding to fluid samples of varying condition, gives an estimate of the relative condition of the fluid sample under test. The test procedure also includes a measurement of the opacity of the fluid sample to visible light, with this measurement being used in conjunction with the calculated quality parameter to more accurately determine the relative condition of the fluid under test. The tester unit may be operated in a stand-alone manner or it may be connected to a computer for storage and display of test results.

10 Claims, 4 Drawing Sheets

METHOD AND APPARATUS FOR SENSING THE CONDITION OF A FLUID

FIELD OF THE INVENTION

This invention relates to a method of determining the condition of a fluid used in a process, such as a lubricating oil used in an internal combustion engine, and to apparatus for practice of that method to determine the condition of such a fluid.

BACKGROUND OF THE INVENTION

Lubricating fluids, such as the motor oil used in internal combustion engines, undergo a significant decrease in their lubricating qualities over the course of their use. This deterioration can be due to many different factors, among these being contamination from other chemicals such as engine coolant, breakdown of chemical additives in the oil, and the increase in oil viscosity due to harsh operating conditions. In order to prevent undue wear and damage to the machines they are intended to protect, lubricants must be replaced before their lubricating qualities diminish to an unacceptable level. Changing the motor oil at a fixed milage or time interval can be very wasteful, since the interval must be based on a conservatively short estimate of the useful life of the oil. Many methods have been proposed in which an electrical characteristic of the lubricant is measured and used to evaluate its lubricating properties.

U.S. Pat. No. 2,752,566 describes a method of checking for chemical and solid particulate contamination in an oil sample by measuring the resistance of the sample to electrical current. Chemical contamination is evaluated by placing electrodes in the sample with a gap distance well in excess of the maximum expected working clearances between parts in the engine. Solid particulate contamination is evaluated with electrodes set at a gap distance approximately equal to or slightly less than the normal working clearances.

U.S. Pat. No. 4,029,554 describes a method in which electrodes made of dissimilar materials are placed in an oil sample, and oxide byproducts present in the oil cause an oxidation reaction to take place with the electrodes. This oxidation reaction produces a corresponding voltage output, and this voltage output is amplified and measured. The greater the amount of oxidation byproducts present in the oil sample, the greater the voltage produced.

U.S. Pat. No. 5,028,144 describes an apparatus for measuring the amount of moisture contamination in brake fluid. This is accomplished by measuring the electrical conductivity of the fluid and comparing it with benchmark values of conductivity obtained from fluid samples with known moisture contents.

U.S. Pat. No. 4,686,857 describes a method in which a short duration DC pulse is applied to two electrodes submerged in the lubricant under test, and the resulting transient response current is detected. Because a direct current is used, the molecules of various contaminants in the oil undergo electrolytic dissociation resulting in a rapid decrease in current flow as the fluid polarizes. In one form of this device, the fluid under test is heated or cooled to a prescribed temperature so that the test results do not show any current variation relating to differences in temperature.

Because of their relatively high cost and complexity, none of these devices have achieved any substantial degree of commercial success and there accordingly exists a need for a reliable low cost, simple, method and apparatus for measuring the quality of lubricating oil and the like.

SUMMARY OF THE INVENTION

The present invention provides a method and apparatus for measuring the condition of a fluid by heating the fluid to an elevated temperature, measuring an electrical characteristic of the fluid at that first temperature, heating the still further, and again measuring the aforesaid electrical characteristic. The two measured values of the electrical characteristic are used to calculate a quality parameter which is compared with quality parameter values corresponding to fluid samples of varying condition.

In the preferred embodiment of the present invention, the electrical characteristic measured is conductivity. The conductivity value is measured by placing a sample of the fluid to be tested in contact with two electrodes, applying an AC voltage across the electrodes, and measuring the resulting induced current. The fluid under test is heated by means of an electric resistance heater.

The preferred embodiment of the invention further includes means for measuring the opacity of the fluid sample to visible light. This measurement is used in conjunction with the calculated quality parameter to more accurately determine the relative condition of the fluid under test.

The tester unit of the present invention is a small, inexpensive, easy to use device which may, if desired, be connected via a serial port to a personal computer for the display or storage of test results.

DETAILED DESCRIPTION OF THE PREFERRED EMBODIMENT

Figure 1:
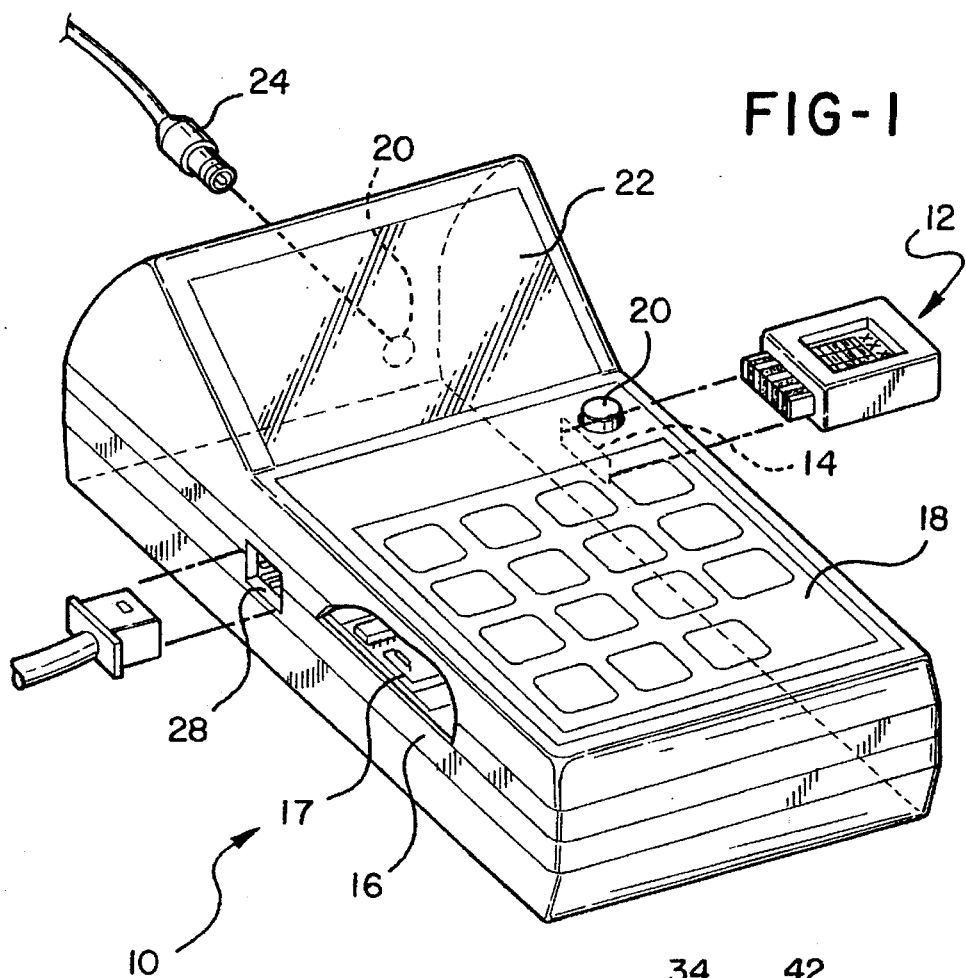
FIG. 1 is a perspective view of the fluid testing device of the present invention showing the sensor unit detached from the tester unit.

Referring to FIG. 1, the testing device of the present invention comprises two main portions: a test unit generally indicated at 10 and a sensor unit generally indicated at 12. Test unit housing 16 encloses and supports a printed circuit board 17 which is comprised of the electronic components which store the test software and execute the test procedure. During use, sensor unit 12 is connected to test unit 10, making physical and electrical contact by means of an edge connector 14 accessible through an opening in the side of the test unit housing 16.

A keypad 18 and an ON/OFF switch 20 are provided on the upper surface of test unit housing 16, these controls permitting user interface with the testing device. A display panel 22 is also provided on upper surface of test unit housing 16. Display panel 22 may be any of the several types of displays commonly used on electronic devices, and in the preferred embodiment is a liquid crystal display.

An external power supply 24 connects to the test unit 10 by means of a jack 26. A serial port 28 is provided by means of which the testing device may be connected to a computer (not shown) for storage and display of test results.

Figure 2:
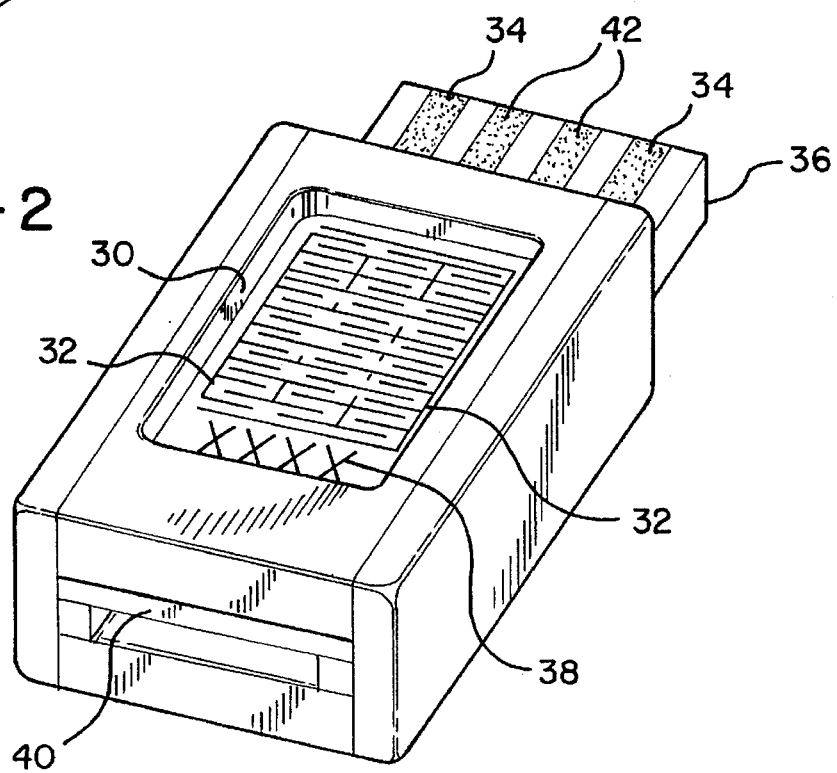
FIG. 2 is a perspective view of the sensor unit.

Referring to FIG. 2, sensor unit 12 is composed of an electrically and thermally insulative material, and is formed with a well 30 in its upper surface to contain the fluid sample during testing. The surface that forms the bottom of the well is provided with a pair of spaced electrodes 32 by means of which the fluid sample is subjected to an AC voltage during the testing procedure. Electrode leads 34 extend from electrodes 32 to a sensor unit connecting tab 36, and make electrical contact with test unit 10 when sensor unit 12 is plugged into edge connector 14. The bottom surface of well 30 is marked with one or more graphic symbols 38 to allow a visual evaluation by the user of the opacity of the fluid sample. A heating element 40 is located below the bottom surface of the well. Electric power is supplied to heating element 40 via electric heater leads 42 which extend onto sensor unit connecting tab 36, and make electrical connection with test unit 10 when sensor 12 is plugged into edge connector 14. Sensor unit 12 is detachable from test unit 10 so that it may be easily emptied and cleaned of fluid after use.

Figure 3:
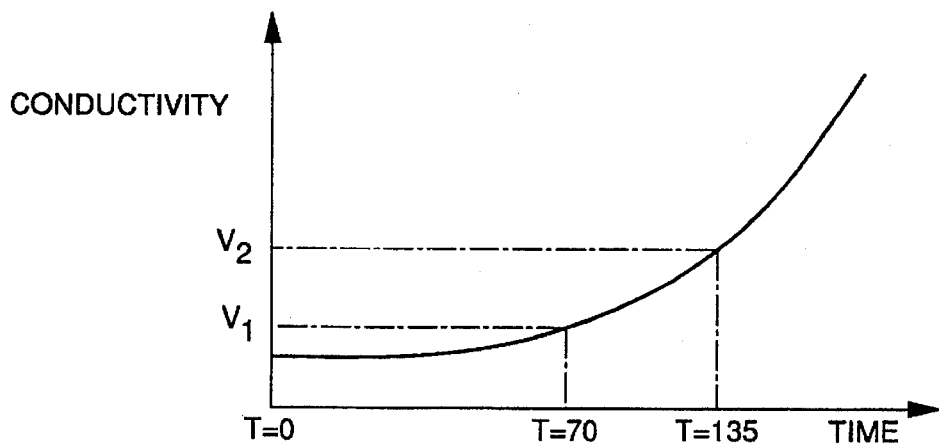
FIG. 3 is a graph showing the increase in induced current measured across a typical fluid sample as it is heated.

The present invention measures conductivity of a fluid sample by applying an alternating current of sine or square-wave waveform to electrodes 32 and detecting the resulting induced current. The conductivity of the fluid is measured continually while the fluid sample is heated by heating element 40, but the tester uses only two discrete values of the conductivity, $V_1$ and $V_2$ (see FIG. 3), to calculate a quality parameter of the fluid. The reading of conductivity $V_1$ is taken at a fixed time, $T_1$, after heating element 40 has switched on and begun to heat the fluid sample. In the preferred embodiment, time $T_1$ is on the order of 70 seconds. Immediately after the $V_1$ reading is taken, the electric voltage supplied to heating element 40 is increased, thereby further increasing the temperature of the fluid sample before the second conductivity reading $V_2$ is taken. In the preferred embodiment of the invention, the reading of $V_2$ is taken on the order of 35 seconds after the $V_1$ reading, at $T_2=105$ seconds. To reduce the effect of any measurement error, the values of $V_1$ and $V_2$ may be obtained by taking a time-average of the conductivity readings over a short period of time.

Figure 3A:
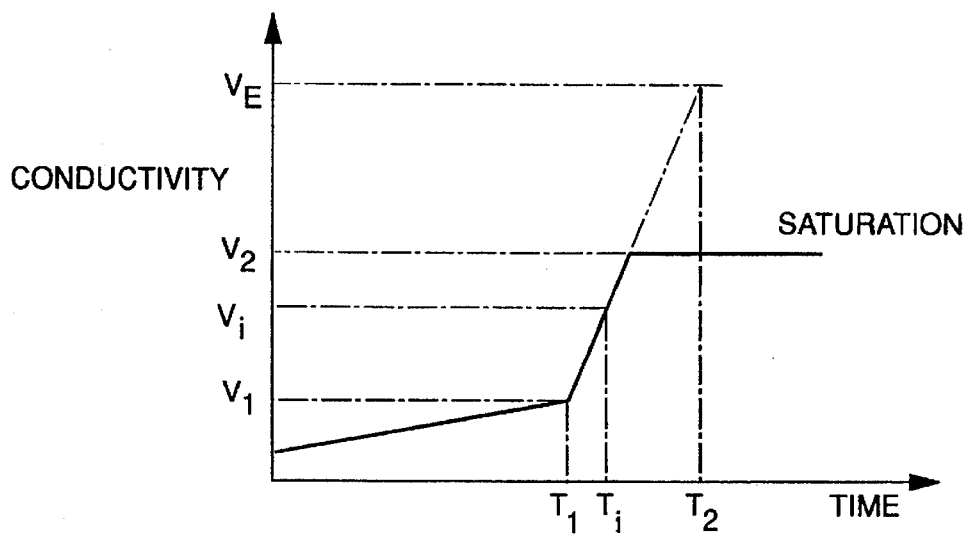
FIG. 3a is a graph showing the linear extrapolation required to estimate the induced current at an elevated temperature when the linear range of the measuring circuit is exceeded.

In some cases, the electrical components making up the conductivity measuring circuit may have a linear range too narrow to permit a valid measurement of the conductivity at $T_2=105$ seconds. In this event, the conductivity time history will exhibit a flattening-off at the circuit saturation point (as shown in FIG. 3a) and the measured value of $V_2$ will be in error. In order to overcome this equipment limitation and obtain a more accurate value of the conductivity at $T_2$, an intermediate measurement of the conductivity, $V_i$ is taken at time $T_i$, and $V_i$ is used along with $V_1$ to linearly extrapolate an estimated conductivity $V_E$. (See FIG. 3a). In the preferred embodiment, the intermediate measurement is taken at approximately $T_i=88$ seconds, as it has been found that this will ensure a $V_i$ measurement that falls within the linear range of the measuring circuit. This method of calculating an estimated $V_E$ is implemented by the test device software if the measured value of $V_2$ is equal to the saturation value of the circuit.

The conductivity values obtained at the two different temperatures are used to calculate a quality parameter, Q, which expresses the relative condition of the fluid sample. The exact function of $V_1$ and $V_2$ used to calculate Q will depend upon the type of fluid being tested, and must be derived by empirical testing. In the case of motor oil used in internal combustion engines, empirical studies have shown a strong correlation between lubricating effectiveness and a quality parameter calculated by the equation:

$$Q = \frac{V_2}{4} + \frac{V_2}{V_1}$$

Many different factors effect the conductivity and hence the Q value of a lubricant. One of these is the breakdown of the antioxidant additives in most oils that occurs during use. As the additives break down, the conductivity of the oil decreases at first, but then begins to increase as the oil oxidizes to form acidic decomposition products. Another factor is contamination of the oil by engine coolant, which can leak into the oil supply as a result of poor seals within the engine. Such coolant contamination results in a drastic increase in electrical conductivity. Since these various factors interact in a complicated manner, a single measurement of conductivity, even if taken at a known, fixed temperature, will not necessarily give a useful indication of fluid condition. By taking into account the change in conductivity that occurs over a temperature range, quality parameter Q has been found to correlate more accurately with fluid condition. The change in conductivity that occurs in a fluid as it undergoes a change in temperature is relatively insensitive to the exact temperatures at which the test is carried out, so precise temperature control of the fluid is not necessary.

Figure 4:
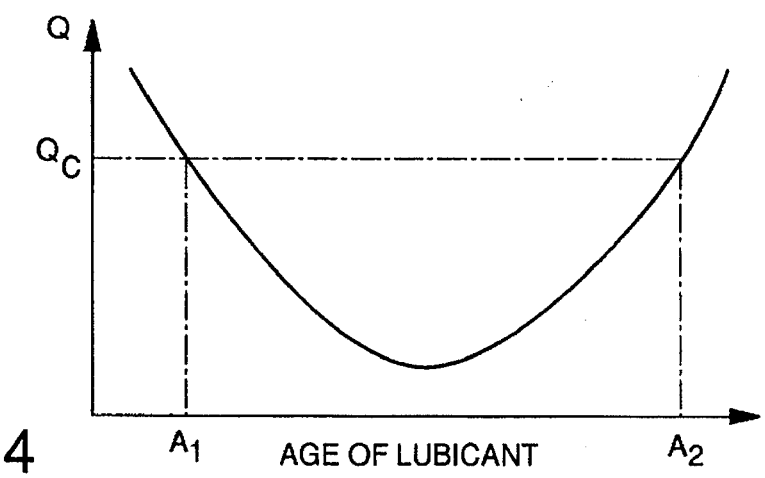
FIG. 4 is a graph showing the change in the quality parameter of a typical fluid sample over the course of its use.

As shown in FIG. 4, new, unused oil will have a relatively high Q value. Over the course of its use, the oil's Q value will initially decrease. At some point during its use the Q value will reach a minimum and then begin to increase again. The shape of this curve is determined by the interaction of the various factors described above. Since any calculated value of $Q_C$ can correspond to an oil sample of two different ages, $A_1$ or $A_2$, an ambiguity occurs. The result of the opacity test conducted at the beginning of the test sequence is used to resolve this ambiguity. If the fluid sample is so opaque that the graphic symbol 38 on the bottom of well 30 cannot be seen by the operator, it is concluded that the fluid sample is old and falls on the upward sloping portion of the curve shown in FIG. 4.

Figure 5:
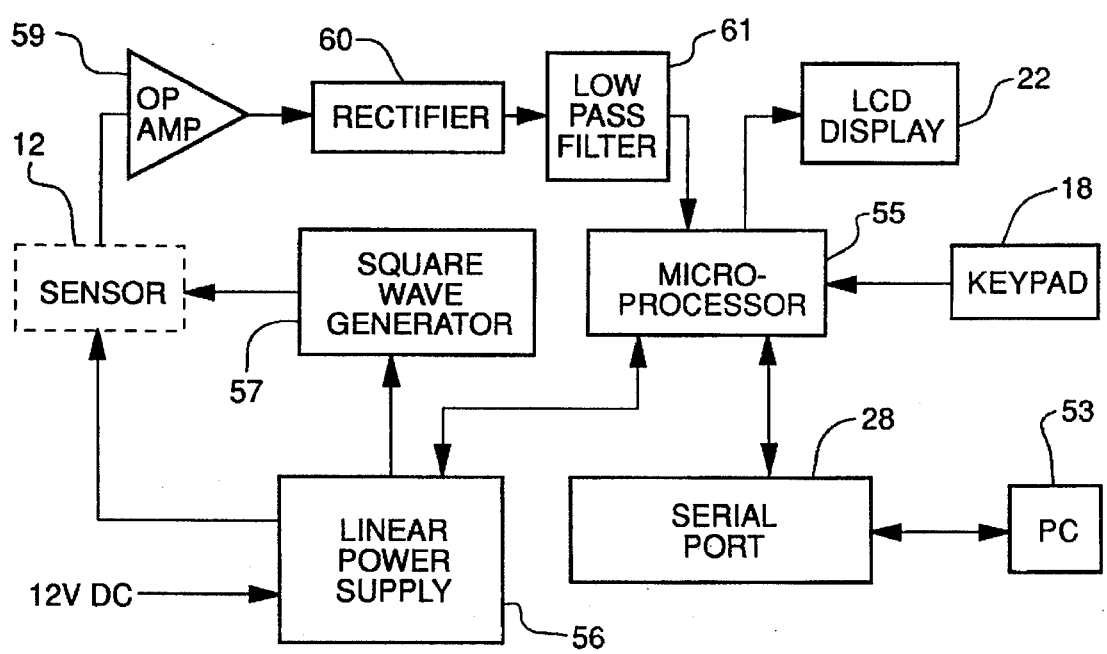
FIG. 5 is a functional block diagram of the circuit of the present invention.

Referring now to FIG. 5, the circuit of the present invention includes a liquid crystal display 22, a keypad 18, and a serial port 14 which provide means for the user to interface with a computer 53. Microprocessor 55 stores the test software, controls the testing program, and processes the test results. A linear power supply 56 accepts 12 volt DC power from an external source and convert it to 7 volt or 8 volt DC (depending on the stage of the test being run) to power heating element 40 on sensor unit 12, as well as 9 volt DC power which is supplied to a square wave generator 57. Square wave generator 57 produces an alternating current which is applied to electrodes 32 on sensor unit 12. The conductivity measured across electrodes 32 is processed through an operational amplifier 59, a rectifier 60 and a low pass filter 61, and passed to microprocessor 55.

Figure 6:
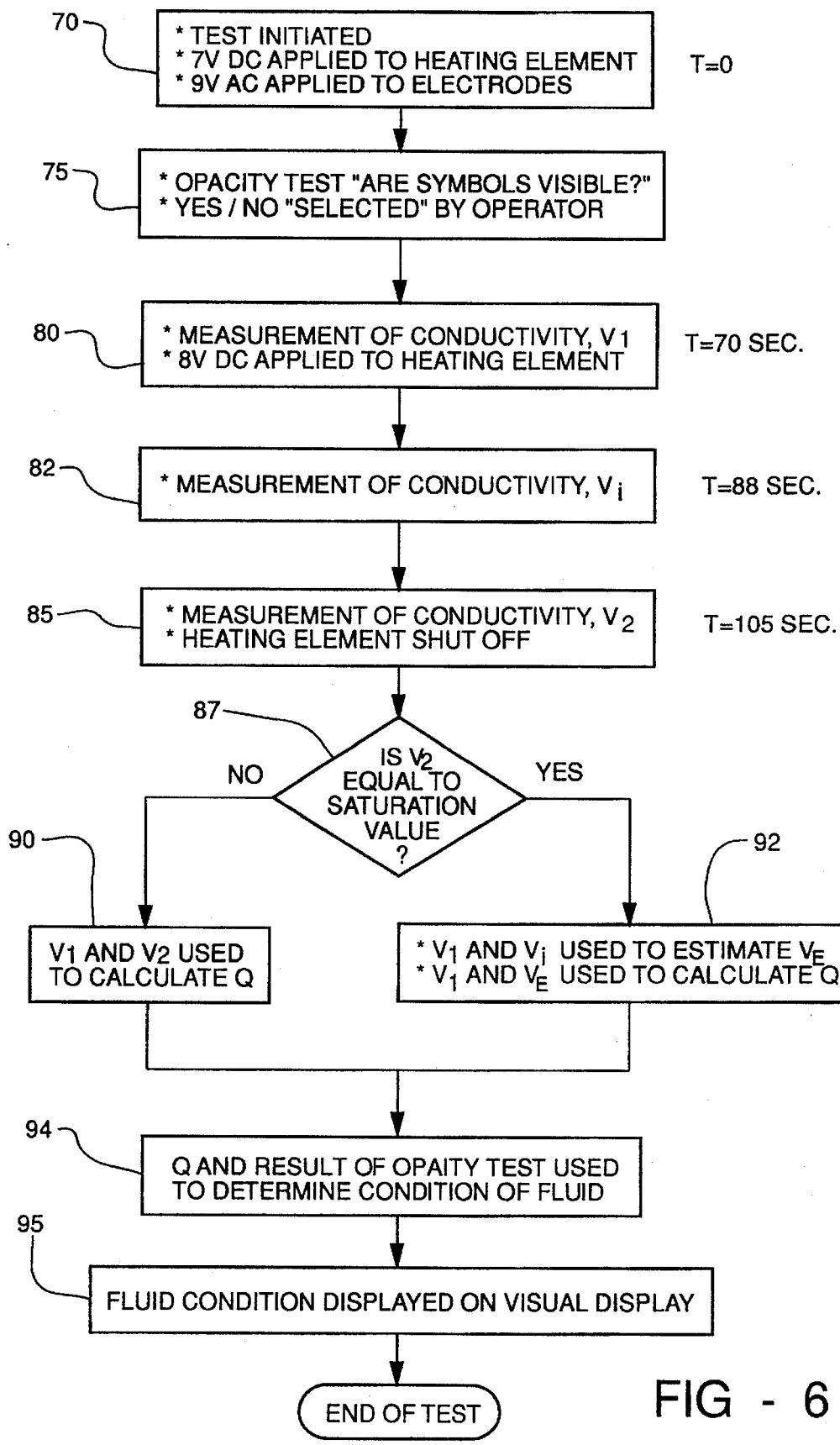
FIG. 6 is a flow chart showing the steps in the fluid condition evaluation method of the present invention.

FIG. 6 outlines the general sequence of steps in the testing procedure. In block 70 the test is initiated by applying a 7 volt DC current to heating element 40 and a 9 volt AC current to the electrodes 32. Reference time T=0 is established. In block 75, the opacity test is performed. The user is queried as to whether the graphic symbols 38 on the sensor unit are visible through the fluid sample, and answers yes or no. In block 80, at T=70 seconds, the first measurement is taken of the conductivity across electrodes 32, and this value is stored as $V_1$. Also at T=70 seconds, the voltage applied to heating element 40 is increased to 8 volts DC.

At T=88 seconds, as shown in block 82, a second measurement of the conductivity is taken to establish $V_i$. In block 85 a third measurement is taken of the conductivity and stored as $V_2$. This occurs at time T=105 seconds, also at which time the power to heating element 40 is shut off. In block 87, the test program compares the stored $V_2$ with a stored saturation value. If $V_2$ is less than the saturation value, $V_1$ and $V_2$ are used to calculate Q (block 90). If $V_2$ is equal to the saturation value, block 92 is implemented and $V_E$ is estimated by linearly extrapolating from $V_1$ and $V_i$. $V_E$ is then used with $V_1$ to calculate Q. Next, in block 94, Q and the result of the opacity test from block 75 are used to determine the relative condition of the fluid. Finally, in block 95, the fluid condition is presented to the user on visual display 22.

It will be apparent that many modifications and variations may be implemented without departing from the scope of the novel concept of this invention.

We claim:

1. A method of evaluating the condition of a fluid comprising:

heating a sample of the fluid;

measuring an electric characteristic of the fluid sample at a first temperature;

measuring the aforesaid electric characteristic of the fluid sample at a second fluid temperature which is higher than the first temperature;

calculating a quality parameter as a function of the measured electric characteristics at the first and second fluid temperatures;

the quality parameter Q being calculated as:

$$Q = \frac{V_2}{4} + \frac{V_2}{V_1}$$

where $V_1$=the conductivity of the fluid sample measured at the first temperature, and $V_2$=the conductivity of the fluid sample measured at the second temperature; and comparing the calculated quality parameter with known quality parameter values corresponding to fluid samples of varying condition.

2. The method of claim 1, in which the measured electric characteristic is conductivity.

3. The method of claim 1, in which the fluid sample is heated by an electric resistance heater.

4. The method of claim 1, in which the electric characteristic is measured by placing the fluid sample in contact with two electrodes.

5. The method of claim 4, in which an AC voltage is applied across the two electrodes, and the resulting current passing through the fluid sample is measured.

6. The method of claim 5, in which the AC voltage is a sine or square waveform.

7. An apparatus for evaluating the quality of a fluid comprising:

fluid containing means for holding a volume of the fluid under evaluation;

electric heater means for increasing the temperature of said fluid;

electrode means applying an AC voltage to said fluid;

means for measuring an electrical characteristic of said fluid at a plurality of fluid temperatures as said fluid increases in temperature, said measuring means being in electrical connection with said electrode means;

means for calculating a quality parameter from electrical characteristic measurements taken by said measuring means;

means for comparing said quality parameter with predetermined reference values of said quality parameter to determine the relative quality of the fluid under evaluation;

means for measuring the opacity to visible light of the fluid under evaluation:

means for combining said opacity measurement with said quality parameter in determining the relative quality of said fluid; and means for visually displaying the results of said relative quality comparison.

8. The apparatus of claim 7 further including means for connecting the apparatus with a computer, for the purpose of displaying results of said comparison on said personal computer.

9. The apparatus of claim 7 wherein said fluid containing means, said heater means, and said electrode means are formed as a unit that may be physically detached from the rest of said apparatus for cleaning after a fluid sample is tested.

10. A method of evaluating the condition of a fluid comprising:

heating a sample of the fluid;

measuring an electric characteristic of the fluid sample at a first temperature;

measuring the aforesaid electric characteristic of the fluid sample at a second fluid temperature which is higher than the first temperature;

calculating a quality parameter as a function of the measured electric characteristics at the first and second fluid temperatures;

comparing the calculated quality parameter with known quality parameter values corresponding to fluid samples of varying condition;

measuring the opacity of the fluid sample to visible light; and using the measurement of opacity in conjunction with the calculated quality parameter to determine the condition of the fluid.

* * * * *